United States Patent

Schwarzmann et al.

[11] 4,004,030
[45] Jan. 18, 1977

[54] MICROBIOCIDALLY EFFECTIVE AMINES OR AMINE MIXTURES

[75] Inventors: Günter Schwarzmann, Essen-Uberruhr; Ulrich Holtschmidt, Essen, both of Germany

[73] Assignee: TH. Goldschmidt AG, Germany

[22] Filed: Dec. 23, 1974

[21] Appl. No.: 535,552

Related U.S. Application Data

[63] Continuation-in-part of Ser. No. 376,962, July 6, 1973, abandoned.

[30] Foreign Application Priority Data

July 11, 1972  Germany ............... 2234017
Sept. 13, 1972  Germany ............... 2244814

[52] U.S. Cl. ............... 424/325; 260/584 R; 71/67
[51] Int. Cl.² ............... A01N 9/20; A01N 9/24
[58] Field of Search ............... 424/325; 260/584 R

[56] References Cited

UNITED STATES PATENTS

| 3,108,036 | 10/1963 | Molnar ............... 424/325 |
| 3,855,297 | 12/1974 | Diana et al. ............... 424/325 |
| 3,872,116 | 3/1975 | Gipson ............... 424/325 |

FOREIGN PATENTS OR APPLICATIONS 2,009,276  5/1971  Germany

OTHER PUBLICATIONS

Fishbein, Modern Women's Medical Encyc. (1959), p. 124.

*Primary Examiner* — V. D. Turner
*Attorney, Agent, or Firm* — James E. Bryan

[57] ABSTRACT

This invention relates to a microbiocidal composition comprising a carrier and a compound having the formula

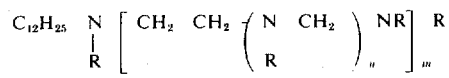

in which
$n$ and $m$ are 0 or 1, and $n$ is 0 if $m$ is 0, and
R is hydrogen or a $-(CH_2)_2OH$ group, at least one R being a $-(CH_2)_2OH$ group. The invention also relates to a process for killing microbes and to certain novel compositions of matter.

14 Claims, No Drawings

MICROBIOCIDALLY EFFECTIVE AMINES OR AMINE MIXTURES

This application is a continuation-in-part of application Ser. No. 376,962, filed July 6, 1973 now abandoned.

The present invention relates to microbiocidally effective compounds or compound mixtures based on alkyl amines or the derivatives thereof.

Microbiocides in the sense of the present invention are understood as compounds effecting the destruction of gram-positive as well as gram-negative bacteria, fungi, yeasts, viruses, and algae.

Known from German Patent No. 862,477, are means for simultaneous body cleansing and disinfection, which consist of an aqueous preparation of salts of any desired inorganic or organic acids with amphoteric compounds corresponding to the general formula

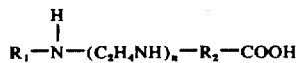

wherein $R_1$ is a hydrocarbon chain of approximately 12 to 18 carbon atoms, $n = 1$, 2, or 3, $R_2 = CH_2$, $C_6H_4$, $C_6H_3OH$, or $CH_2 - C_6H_3OH$.

Known from German Patent No. 1,041,627, is the use of amphoteric surface-active compounds having the formula

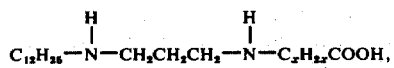

wherein

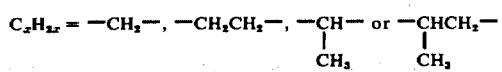

and the water-soluble salts thereof with acids, as washing and disinfecting agents.

Compounds of the aforementioned type have been proven to be satisfactory in the past as agents having microbiocidal properties.

It now has been surprisingly found that compounds or compound mixtures having an increased microbiocidal effect can be obtained, according to the present invention, by reacting at least one compound, having the general formula

wherein X is

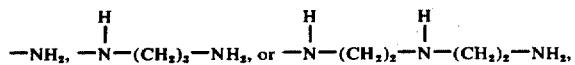

either with ethylene chlorohydrin in a molar quantitative ratio of 1:0.5 to 1:2 in the presence of hydrogen chloride acceptors which, based upon halogenated alcohol, are added in approximately equimolar amounts, in an aqueous or alcoholic medium at temperatures of 50° to 150° C, and by separating, if necessary, the salts produced during the reaction in a manner known per se; or by reacting the same with ethylene oxide in a molar quantitative ratio of 1:0.5 to 1:2 at elevated temperatures, preferably at temperatures of 50° to 130° C.

Even though the reaction of the amino-compounds with ethylene chlorohydrin or ethylene oxide may be carried out in molar quantitative ratio of 1:0.5 to 1:2, the reaction in a quantitative molar ratio of approximately 1:1 is especially preferred.

If, during the reaction with ethylene chlorohydrin, a lower alcohol is employed as a reaction medium, preferably n-propanol, and an alkali hydroxide is employed as the acid acceptor, preferably sodium hydroxide, the alkali chlorides formed during the reaction are obtained in a form which is practically insoluble in the reaction medium and may be separated from the reaction medium by filtration. If the reaction is conducted in an aqueous medium, the alkali chlorides remain in solution. It is not necessary to remove these salts from the reaction mixture since as a practical matter they do not affect the microbiocidal efficacy of the products of the process. However, for purposes of assuring the purity of the desired reaction product, the separation of the salts formed during the reaction is preferred and the reaction therefore preferably is carried out in an alcoholic medium. One advantage of the salt-free solutions also is the reduction of the corrosion which is caused by these salts in apparatus, dosing devices, piping, metallic barrels, and the like.

When ethylene chlorohydrin is employed, alkaline earth hydroxides — as well as the alkali hydroxides — are used as acid acceptors. Instead of the hydroxides, the corresponding carbonates or bicarbonates also may be employed.

Preferred as a reaction medium is n-propanol, as has been mentioned hereinabove. Other particularly suitable lower alcohols are ethanol, i-propanol, and butanol.

During the reaction with ethylene oxide, temperatures of 105° to 115° C are preferred.

The microbiocidally effective compounds of the present invention have the general formula

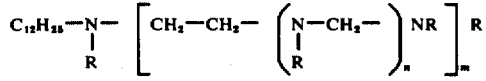

in which $n$ and $m$ are 0 or 1, and $n$ is 0 is $m$ is 0, and
R is hydrogen or a $-(CH_2)_2OH$ group, at least one R being a $-(CH_2)_2OH$ group.

Certain of these compounds are new and have the general formula

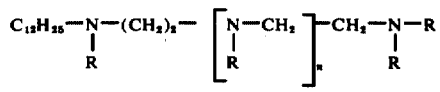

in which $n$ is 0 or 1, and

R is hydrogen or a —(CH$_2$)$_2$OH group, at least one R being a —(CH$_2$)$_2$OH group.

The compounds and/or compound mixtures obtained, which also may contain unreacted amine and amine derivatives, may be packaged for use in any desired manner. They may be marketed as concentrated aqueous or alcoholic solutions. They additionally may contain odorous substances or other additions, such as dyes, for example. The compounds also may be dissolved in fluorinated chlorinated hydrocarbons and used in aerosol form.

It is possible to admix with the compounds obtained according to the present invention, which are themselves surface-active, additional cationactive or non-ionogenic tensides. The cleansing effect can be particularly improved thereby. If one adds to the products obtained according to the present invention water-soluble, non-ionogenic tensides, such as, for example, addition products of ethylene oxide to naturally or synthetically produced alcohols, one can observe in addition to the improved cleansing effect also an increase of the microbiocidal effect.

The process of the present invention will be further illustrated on the basis of the following examples. Thereafter, the efficacy of the inventively prepared compounds and/or compound mixtures will be shown in the form of tables. The investigation relative to microbiocides was carried out according to the rules and regulations of the Deutschen Gesellschaft fuer Hygiene und Mikrobiologie e.V. (the German Society for Hygiene and Microbiology) Gustav Fischer Editor, Stuttgart, 1959. In the tables, the symbol + signifies germ growth, the symbol - signifies no germ growth.

EXAMPLE 1

Reaction of C$_{12}$H$_{25}$NH$_2$ with ClCH$_2$—CH$_2$—OH in a molar ratio of 1:1

Placed in a 2 liter four-necked flask, equipped with stirrer, reflux cooler, thermometer and dropping funnel, are 1 mole (185 grams) of C$_{12}$H$_{25}$NH$_2$ and 1 mole (40 grams) of NaOH in 500 grams of n-propanol and the mixture is heated to 50° C. While vigorously stirring, 1 mole (81 grams) of ClCH$_2$—CH$_2$—OH is slowly added dropwise and reacted thereafter for another hour at reflux. Thereafter, the reaction mixture is allowed to cool and precipitated NaCl (56 grams =0.97 mole) is separated. The filtrate thus yielded (790 grams) contains 230 grams of the active material mixture. The solution thus has an active material content of 29.1% by weight.

EXAMPLE 2

Reaction of

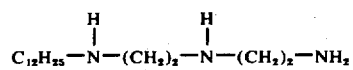

with ClCH$_2$—CH$_2$—OH in a molar ration of 1 : 0.5

Placed in a 2 liter four-necked flask, equipped with stirrer, reflux cooler, thermometer and dropping funnel, are 1 mole (272 grams) of

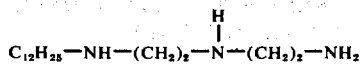

and 0.5 mole (28 grams) of KOH in 500 grams of i-propanol. While stirring, 0.5 mole (40 grams) of ClCH$_2$—CH$_2$—OH is slowly added dropwise, and thereafter stirring is effected for approximately 2 more hours at 80° C. After cooling the reaction mixture, the precipitated KCl is separated in a Buchner funnel, and washing is effected with i-propanol. The KCl is dried and weighed. Obtained are 32 grams of KCl (0.43 mole). The filtrate thus yielded (850 grams) contains 294 grams of the active material mixture. The solution thus has an active material content of 34.6% by weight.

The reaction product has the formula

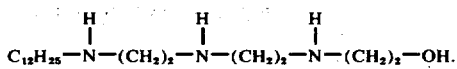

EXAMPLE 3

Reaction of

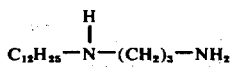

with ClCH$_2$—CH$_2$—OH in a molar ratio of 1 : 1

Placed in a 2 liter four-necked flask, equipped with stirrer, reflux cooler, thermometer and dropping funnel, are 1 mole (243 grams)

and 1 mole of NaOH (40 grams) in 500 ml of water, and the mixture is heated to 70° C while vigorously stirring. Thereafter, 1 mole (81 grams) of ClCH$_2$—CH$_2$—OH are slowly added dropwise and thereafter reaction is effected for another hour under reflux. Obtained in this manner are 770 ml of a solution which contains 287 grams of effective substance. The solution thus has 37.3% by weight of effective substance.

The reaction product has the formula

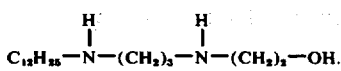

EXAMPLE 4

Reaction of a mixture of 1 part of

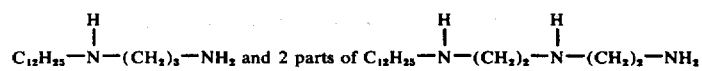

with ClCH$_2$—CH$_2$—OH in a molar ratio of 1 : 1

Placed in a 2 liter four-necked flask, equipped with stirrer, reflux cooler, thermometer, and dropping funnel, are 0.33 mole (81 grams) of

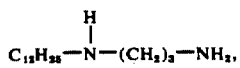

0.67 mole (181 grams)

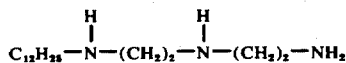

and 1 mole (40 grams) of NaOH in 500 grams of n-propanol, and the mixture is heated to 50° C. While stirring, 1 mole (81 grams) of ClCH$_2$—CH$_2$—OH is added in small portions and stirring is continued for about 3 hours at room temperature. The NaCl, which is insoluble in the reaction mixture, is separated out in a Buchner funnel, washed with n-propanol, and dried. Thus obtained are 57 grams (0.98 mole) of NaCl. In the collected filtrate (866 grams) there are 306 grams of the active substance mixture. The solution thus has 35.3% by weight of active substance

EXAMPLE 5

Reaction of C$_{12}$H$_{25}$NH$_2$ with

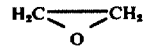

in a molar ratio of 1 : 1

371 grams of C$_{12}$H$_{25}$NH$_2$ (2 moles) are placed in an autoclave and flushed with nitrogen. Thereafter, heating to 110° C is effected. Then, 88 grams of ethylene oxide (2 moles) are added, under pressure, in three portions. A pressure of approximately 9 atmospheres prevails in the autoclave. After the ethylene oxide addition has been completed, reaction is continued for one hour. Thereafter, the cooled reaction mixture is filtered and 440 grams of a clear liquid are obtained which are subjected to a fractional distillation. Obtained are the following fractions:

I. 114 grams (=25.9%) of unreacted C$_{12}$H$_{25}$NH$_2$,
   Boiling point: 119° – 124° C/0.1 Torr II. 221 grams (=50.2%) of

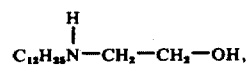

Boiling point: 141° – 145° C/0.1 Torr

Elemental analysis for C$_{14}$H$_{31}$ON:

| | calculated | | found |
|---|---|---|---|
| C | 73.3% by weight | C | 73.1% by weight |
| H | 13.6% by weight | H | 13.9% by weight |
| O | 7.0% by weight | O | 6.9% by weight |
| N | 6.1% by weight | N | 6.4% by weight |

III. Residue: 80 grams

EXAMPLE 6

Reaction of

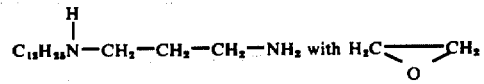

at a molar ratio of 1 : 1

550 grams of

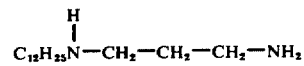

(2.25 moles) are placed in an autoclave, flushed with nitrogen, and heated to 105° to 115° C. Thereafter, 100 grams of ethylene oxide (2.25 moles) are added, under pressure, in three portions. A pressure of 9 to 10 atmospheres then will prevail in the autoclave. After the addition of ethylene oxide, reaction is continued for another 2 hours. Thereupon, the reaction product is filtered. Obtained are 614 grams of a light yellow viscous liquid which is subjected to a fractional distillation. The following fractions are obtained:

I. 200 grams (=32.6%) of unreacted

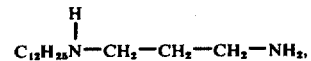

Boiling point: 111° – 114° C/10$^{-2}$ Torr.

II. 216 grams (=35.3%) of

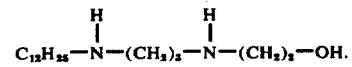

Boiling point: 160° –166° C/10$^{116\ 2}$ Torr.

Elemental analysis for C$_{17}$H$_{38}$ON$_2$:

| | calculated | | found |
|---|---|---|---|
| C | 71.4% by weight | C | 71.6% by weight |
| H | 13.3% by weight | H | 12.7% by weight |
| O | 5.6% by weight | O | 5.8% by weight |
| N | 9.7% by weight | N | 9.3% by weight |

III. 143 grams (=23.3%) of

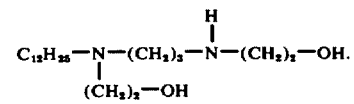

Boiling point: 178— 183° C/10$^{-2}$ Torr.

Elemental analysis for C$_{19}$H$_{42}$O$_2$N$_2$

| | calculated | | found |
|---|---|---|---|
| C | 69.2% by weight | C | 69.7% by weight |
| H | 12.8% by weight | H | 12.6% by weight |
| O | 9.6% by weight | O | 9.3% by weight |
| N | 8.4% by weight | N | 8.2% by weight |

IV. 21 grams (=3.0%) of residue, composed of

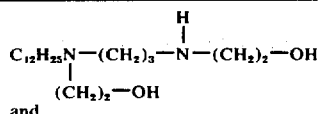
and
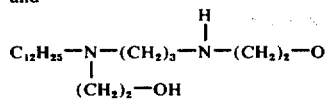

Elemental analysis:

| | calculated for $C_{19}H_{42}O_2N_2$ | | calculated for $C_{21}H_{46}O_3N_2$ | | found |
|---|---|---|---|---|---|
| C | 69.2% by weight | C | 67.4% by weight | C | 69.4% by weight |
| H | 12.8% by weight | H | 12.4% by weight | H | 12.1% by weight |
| O | 9.6% by weight | O | 12.8% by weight | O | 10.8% by weight |
| N | 8.4% by weight | N | 7.0% by weight | N | 7.2% by weight |

EXAMPLE 7

Reaction of

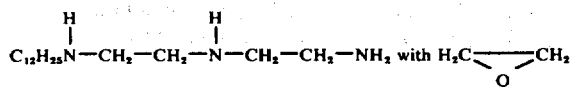

in a molar ratio of 1 : 1
493 grams of

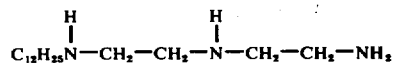

(1.8 moles) are placed in an autoclave, flushed with nitrogen, and heated to 105° to 115° C. Thereafter 80 grams of ethylene oxide (1.8 moles) are added, under pressure, in three portions. A pressure of from 9 to 10 atmospheres then will prevail in the autoclave. After the addition of ethylene oxide, reaction is continued for another 2 hours. Thereafter, the reaction product is filtered. Obtained are 518 grams of an almost colorless liquid which is subjected to a fractional distillation. The following fractions are produced:

I. 183 grams (=35.2%) of unreacted

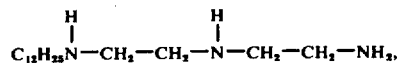

Boiling point: 120° – 124° C/$10^{-2}$ Torr.

II. 178 grams (=34.4%) of

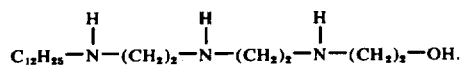

Boiling point: 132° – 134° C/$10^{-2}$ Torr.

Elemental analysis for $C_{18}H_{41}ON_3$:

| | calculated | | found |
|---|---|---|---|
| C | 68.7% by weight | C | 68.7% by weight |
| H | 13.0% by weight | H | 12.7% by weight |
| O | 5.1% by weight | O | 5.4% by weight |
| N | 13.3% by weight | N | 13.1% by weight |

III. 114 grams (=22.0%) of

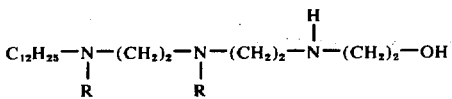

in which one R is hydrogen and one R is the —$CH_2CH_2OH$ group.

Boiling point: 180° – 188° C/$10^{-2}$ Torr.

Elemental analysis for $C_{20}H_{45}O_2N_3$:

| | calculated | | found |
|---|---|---|---|
| C | 66.9% by weight | C | 68.0% by weight |
| H | 12.6% by weight | H | 12.6% by weight |
| O | 8.9% by weight | O | 8.3% by weight |
| N | 11.6% by weight | N | 10.7% by weight |

IV. 26 grams (=5%) of residue composed of $$C_{12}H_{25}-N-(CH_2)_2-N-(CH_2)_2-N-(CH_2)_2-OH$$
$$\quad\quad\quad\quad\quad\quad R \quad\quad\quad R \quad\quad\quad H$$

in which one R is hydrogen and one R is the —$CH_2CH_2OH$ group, and $$C_{12}H_{25}-N-(CH_2)_2-N-(CH_2)_2-N(\text{H, }(CH_2)_2-OH)$$
$$\quad\quad\quad (CH_2)_2-OH \quad (CH_2)_2-OH$$

Elemental analysis:

| | calculated for $C_{20}H_{45}O_2N_3$ | | calculated for $C_{22}H_{49}O_3N_3$ | | found |
|---|---|---|---|---|---|
| C | 66.9% by weight | C | 65.3% by weight | C | 67.0% by weight |
| H | 12.6% by weight | H | 12.3% by weight | H | 11.6% by weight |
| O | 8.9% by weight | O | 11.9% by weight | O | 8.5% by weight |
| N | 11.6% by weight | N | 10.4% by weight | N | 9.5% by weight |

Bacteriological investigations

The bacteriological investigations were carried out according to the "Richtlinien fuer die Pruefung Chemischer Desinfektionsmittel" (Guidelines for the Examination of Chemical Disinfecting Agents) of the German Society for Hygiene and Microbiology e.V., Gustav Fischer Editor, Stuttgart, 1959, with the exception that for preparing the respective dilutions, ordinary tap water rather than distilled water was used. The pH value was set in each case with acetic acid.

Table 1

The solution prepared according to Example 1 is diluted with tap water to an extent such that the solution adjusted with acetic acid to a pH value of 7.6 contains 0.1% by weight of active substance.

| Test strain | Concentration in % | Time of action in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | + | + | + | − | − | − |
| | 0.005 | + | + | + | + | − | − |
| | 0.001 | + | + | + | + | + | + |
| E. coli | 0.1 | − | − | − | − | − | − |
| | 0.05 | − | − | − | − | − | − |
| | 0.01 | + | + | − | − | − | − |
| | 0.005 | + | + | + | + | + | + |
| | 0.001 | + | + | + | + | + | + |
| P. vulgaris | 0.1 | − | − | − | − | − | − |
| | 0.05 | − | − | − | − | − | − |
| | 0.01 | − | − | − | − | − | − |
| | 0.005 | + | + | + | + | + | − |
| | 0.001 | + | + | + | + | + | + |
| P. aeruginose | 0.1 | − | − | − | − | − | − |
| | 0.05 | − | − | − | − | − | − |
| | 0.01 | − | + | + | + | + | + |
| | 0.005 | − | + | + | + | + | + |
| | 0.001 | − | + | + | + | + | + |

Table 2

The solution prepared according to Example 2 is diluted with tap water to an extent such that the solution adjusted with acetic acid to a pH value of 7.5 contains 0.1% by weight of active substance.

| Test strain | Concentration in % | Time of action in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | + | − | − | − | − | − |
| | 0.005 | + | + | − | − | − | − |
| | 0.001 | + | + | + | + | − | − |
| E. coli | 0.1 | − | − | − | − | − | − |
| | 0.05 | + | − | − | − | − | − |
| | 0.01 | + | + | + | − | − | − |
| | 0.005 | + | + | + | + | + | + |
| | 0.001 | + | + | + | + | + | + |
| P. aeruginosa | 0.1 | − | − | − | − | − | − |
| | 0.05 | − | − | − | − | − | − |
| | 0.01 | + | − | − | − | − | − |
| | 0.005 | + | + | − | − | − | − |
| | 0.001 | + | + | + | + | − | + |
| C. albicans | 0.1 | + | + | − | − | − | − |
| | 0.05 | + | + | − | − | − | − |
| | 0.01 | + | + | + | + | − | − |
| | 0.005 | + | + | + | + | + | + |
| | 0.001 | + | + | + | + | + | + |
| T. mentagrophytes | 0.1 | − | − | − | − | − | − |
| | 0.05 | − | − | − | − | − | − |
| | 0.01 | + | + | − | − | − | − |
| | 0.005 | + | + | + | − | − | − |
| | 0.001 | + | + | + | + | − | − |

Table 3

The solution prepared according to Example 3 is diluted by the addition of acetic acid to an extent such that the dilution to 0.1% by weight has a pH value of 7.6.

| Test strain | Concentration in % | Time of action in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | + | + | + | − | − | − |
| | 0.005 | + | + | + | + | − | − |
| | 0.001 | + | + | + | + | + | + |
| E. coli | 0.1 | − | − | − | − | − | − |
| | 0.05 | − | − | − | − | − | − |
| | 0.01 | + | − | − | − | − | − |
| | 0.005 | + | + | + | − | − | − |
| | 0.001 | + | + | + | + | + | + |
| P. vulgaris | 0.1 | − | − | − | − | − | − |
| | 0.05 | + | − | − | − | − | − |
| | 0.01 | + | + | + | − | − | − |
| | 0.005 | + | + | + | + | − | − |
| | 0.001 | + | + | + | + | + | + |
| P. aeruginosa | 0.1 | − | − | − | − | − | − |
| | 0.05 | − | − | − | − | − | − |
| | 0.01 | − | − | − | − | − | − |
| | 0.005 | + | + | + | − | − | − |
| | 0.001 | + | + | + | + | + | + |
| C. albicans | 0.1 | − | − | − | − | − | − |
| | 0.05 | − | − | − | − | − | − |
| | 0.01 | − | − | − | − | − | − |
| | 0.005 | + | − | − | − | − | − |
| | 0.001 | + | + | + | + | + | + |

Table 4

The solution prepared according to Example 4 is diluted with the addition of acetic acid to an extent such that the dilution to 0.1% by weight has a pH value of 7.5.

| Test strain | Concentration in % | Time of action in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | + | + | + | − | − | − |
| | 0.005 | + | + | + | + | − | − |
| | 0.001 | + | + | + | + | + | + |
| E. coli | 0.1 | − | − | − | − | − | − |
| | 0.05 | − | − | − | − | − | − |
| | 0.01 | + | + | − | − | − | − |
| | 0.005 | + | + | + | + | − | − |
| | 0.001 | + | + | + | + | + | + |
| P. vulgaris | 0.1 | − | − | − | − | − | − |
| | 0.05 | − | − | − | − | − | − |
| | 0.01 | + | + | + | + | − | − |
| | 0.005 | + | + | + | + | + | − |
| | 0.001 | + | + | + | + | + | + |
| P. aeruginosa | 0.1 | − | − | − | − | − | − |
| | 0.05 | − | − | − | − | − | − |
| | 0.01 | + | − | − | − | − | − |
| | 0.005 | + | − | − | − | − | − |
| | 0.001 | + | + | + | + | + | + |

Table 5

The reaction mixture prepared according to Example 6 is diluted to 0.1% by weight of active substance and adjusted with acetic acid to a pH value of 7.6.

| Test strain | Concentration in % | Time of action in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | + | + | + | − | − | − |

-continued

| Test strain | Concentration in % | Time of action in minutes | | | | | |
|---|---|---|---|---|---|---|---|
| | | 1 | 2 | 5 | 10 | 20 | 30 |
| | 0.005 | + | + | + | + | − | − |
| | 0.001 | + | + | + | + | + | + |
| E. coli | 0.1 | − | − | − | − | − | − |
| | 0.05 | − | − | − | − | − | − |
| | 0.01 | + | − | − | − | − | − |
| | 0.005 | + | + | − | − | − | − |
| | 0.001 | + | + | + | + | + | + |
| P. vulgaris | 0.1 | − | − | − | − | − | − |
| | 0.05 | − | − | − | − | − | − |
| | 0.01 | + | + | + | − | − | − |
| | 0.005 | + | + | + | + | − | − |
| | 0.001 | + | + | + | + | + | + |
| P. aeruginosa | 0.1 | − | − | − | − | − | − |
| | 0.05 | − | − | − | − | − | − |
| | 0.01 | − | − | − | − | − | − |
| | 0.005 | + | + | + | − | − | − |
| | 0.001 | + | + | + | + | + | + |
| P. expansum | 0.1 | − | − | − | − | − | − |
| | 0.05 | − | − | − | − | − | − |
| | 0.01 | + | − | − | − | − | − |
| | 0.005 | + | + | + | − | − | − |
| | 0.001 | + | + | + | + | + | + |

Table 6

The compound II of formula

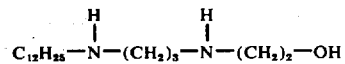

of the reaction mixture prepared according to Example 6 is diluted to 0.1% by weight of active substance and adjusted with acetic acid to a pH value of 7.5.

| Test strain | Concentration in % | Time of action in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | + | + | + | − | − | − |
| | 0.005 | + | + | + | + | − | − |
| | 0.001 | + | + | + | + | + | + |
| E. coli | 0.1 | − | − | − | − | − | − |
| | 0.05 | − | − | − | − | − | − |
| | 0.01 | + | − | − | − | − | − |
| | 0.005 | + | + | − | − | − | − |
| | 0.001 | + | + | + | + | + | + |
| P. vulgaris | 0.1 | − | − | − | − | − | − |
| | 0.05 | − | − | − | − | − | − |
| | 0.01 | + | + | + | − | − | − |
| | 0.005 | + | + | + | + | − | − |
| | 0.001 | + | + | + | + | + | + |
| P. aeruginosa | 0.1 | − | − | − | − | − | − |
| | 0.05 | − | − | − | − | − | − |
| | 0.01 | − | − | − | − | − | − |
| | 0.005 | + | + | + | + | + | + |
| | 0.001 | + | + | + | + | + | + |
| A. flavus | 0.1 | + | + | − | − | − | − |
| | 0.05 | + | + | − | − | − | − |
| | 0.01 | + | + | + | + | − | − |
| | 0.005 | + | + | + | + | − | − |
| | 0.001 | + | + | + | + | + | + |

Table 7

The compound III of formula

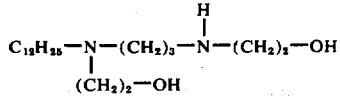

of the reaction mixture prepared according to Example 6 is diluted to 0.1% by weight of active substance and adjusted with acetic acid to a pH value of 7.3.

| Test strain | Concentration in % | Time of action in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | + | + | + | − | − | − |
| | 0.005 | + | + | + | + | − | − |
| | 0.001 | + | + | + | + | + | + |
| E. coli | 0.1 | − | − | − | − | − | − |
| | 0.05 | − | − | − | − | − | − |
| | 0.01 | + | + | + | + | + | + |
| | 0.005 | + | + | + | + | + | + |
| | 0.001 | + | + | + | + | + | + |
| P. vulgaris | 0.1 | − | − | − | − | − | − |
| | 0.05 | − | − | − | − | − | − |
| | 0.01 | + | + | + | + | − | − |
| | 0.005 | + | + | + | + | + | + |
| | 0.001 | + | + | + | + | + | + |
| P. aeruginosa | 0.1 | − | − | − | − | − | − |
| | 0.05 | − | − | − | − | − | − |
| | 0.01 | + | + | + | + | + | + |
| | 0.005 | + | + | + | + | + | + |
| | 0.001 | + | + | + | + | + | + |
| P. expansum | 0.1 | − | − | − | − | − | − |
| | 0.05 | − | − | − | − | − | − |
| | 0.01 | + | + | + | − | − | − |
| | 0.005 | + | + | + | − | − | − |
| | 0.001 | + | + | + | + | + | + |

Table 8

A mixture of

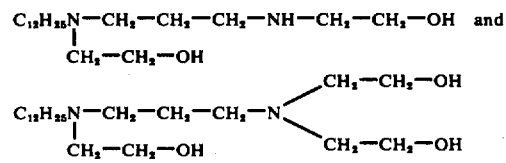

in a molar ratio of approximately 1:1 (from the components obtained according to Example 6) is diluted to 0.1% by weight of active substance and adjusted with acetic acid to a pH value of 6.0.

| Test strain | Concentration in % | Time of action in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.1 | + | + | − | − | − | − |
| | 0.005 | + | + | + | + | − | − |
| | 0.001 | + | + | + | + | + | + |
| E. coli | 0.1 | + | − | − | − | − | − |
| | 0.05 | + | + | − | − | − | − |
| | 0.01 | + | + | + | + | + | + |
| | 0.005 | + | + | + | + | + | + |
| | 0.001 | + | + | + | + | + | + |
| P. vulgaris | 0.1 | + | + | − | − | − | − |
| | 0.05 | + | + | − | − | − | − |
| | 0.01 | + | + | + | + | + | + |
| | 0.005 | + | + | + | + | + | + |

-continued

| Test strain | Concentration in % | Time of action in minutes | | | | | |
|---|---|---|---|---|---|---|---|
| | | 1 | 2 | 5 | 10 | 20 | 30 |
| | 0.001 | + | + | + | + | + | + |
| P. aeruginosa | 0.1 | − | − | − | − | − | − |
| | 0.05 | − | − | − | − | − | − |
| | 0.01 | + | + | + | + | + | + |
| | 0.005 | + | + | + | + | + | + |
| | 0.001 | + | + | + | + | + | + |

Table 9

The reaction mixture prepared according to Example 7 is diluted to 0.1% by weight of active substance and adjusted with acetic acid to a pH value of 7.6.

| Test strain | Concentration in % | Time of action in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | + | + | − | − | − | − |
| | 0.005 | + | + | + | + | − | − |
| | 0.001 | + | + | + | + | + | + |
| E. coli | 0.1 | − | − | − | − | − | − |
| | 0.05 | − | − | − | − | − | − |
| | 0.01 | + | + | − | − | − | − |
| | 0.005 | + | + | + | + | + | − |
| | 0.001 | + | + | + | + | + | + |
| P. vulgaris | 0.1 | + | − | − | − | − | − |
| | 0.05 | + | − | − | − | − | − |
| | 0.01 | + | + | + | + | − | − |
| | 0.005 | + | + | + | + | + | + |
| | 0.001 | + | + | + | + | + | + |
| P. aeruginosa | 0.1 | − | − | − | − | − | − |
| | 0.05 | − | − | − | − | − | − |
| | 0.01 | − | − | − | − | − | − |
| | 0.005 | + | + | + | + | + | + |
| | 0.001 | + | + | + | + | + | + |
| P. expansum | 0.1 | − | − | − | − | − | − |
| | 0.05 | + | − | − | − | − | − |
| | 0.01 | + | + | + | + | − | − |
| | 0.005 | + | + | + | + | + | − |
| | 0.001 | + | + | + | + | + | + |

Table 10

The compound II of formula

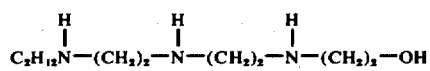

of the reaction mixture prepared according to Example 7 is diluted to 0.1% by weight of active substance and adjusted with acetic acid to a pH value of 7.8.

| Test strain | Concentration in % | Time of action in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | + | + | + | − | − | − |
| | 0.005 | + | + | + | − | − | − |
| | 0.001 | + | + | + | + | + | + |
| E. coli | 0.1 | − | − | − | − | − | − |
| | 0.05 | − | − | − | − | − | − |
| | 0.01 | + | − | − | − | − | − |

| Test strain | Concentration in % | Time of action in minutes | | | | | |
|---|---|---|---|---|---|---|---|
| | | 1 | 2 | 5 | 10 | 20 | 30 |
| | 0.005 | + | + | − | − | − | − |
| | 0.001 | + | + | + | + | + | + |
| P. vulgaris | 0.1 | − | − | − | − | − | − |
| | 0.05 | − | − | − | − | − | − |
| | 0.01 | + | + | − | − | − | − |
| | 0.005 | + | + | + | + | − | − |
| | 0.001 | + | + | + | + | + | + |
| P. aeruginosa | 0.1 | − | − | − | − | − | − |
| | 0.05 | − | − | − | − | − | − |
| | 0.01 | − | − | − | − | − | − |
| | 0.005 | + | + | − | − | − | − |
| | 0.001 | + | + | + | + | + | + |
| C. albicans | 0.1 | + | − | − | − | − | − |
| | 0.05 | + | − | − | − | − | − |
| | 0.01 | + | + | − | − | − | − |
| | 0.005 | + | + | + | − | − | − |
| | 0.001 | + | + | + | + | + | + |

Table 11

The compound III of formula

where one R is hydrogen and one R is the group —(CH$_2$)$_2$OH, of the reaction mixture prepared according to Example 7 is diluted to 0.1% by weight of active substance and adjusted with acetic acid to a pH value of 7.7.

| Test strain | Concentration in % | Time of action in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | + | − | − | − | − | − |
| | 0.005 | + | + | − | − | − | − |
| | 0.001 | + | + | + | + | − | − |
| E. coli | 0.1 | − | − | − | − | − | − |
| | 0.05 | − | − | − | − | − | − |
| | 0.01 | + | − | − | − | − | − |
| | 0.005 | + | + | + | + | + | − |
| | 0.001 | + | + | + | + | + | + |
| P. vulgaris | 0.1 | − | − | − | − | − | − |
| | 0.05 | + | − | − | − | − | − |
| | 0.01 | + | + | + | + | − | − |
| | 0.005 | + | + | + | + | + | + |
| | 0.001 | + | + | + | + | + | + |
| P. aeruginosa | 0.1 | − | − | − | − | − | − |
| | 0.05 | − | − | − | − | − | − |
| | 0.01 | + | + | − | − | − | − |
| | 0.005 | + | + | + | + | + | + |
| | 0.001 | + | + | + | + | + | + |

Table 12

A mixture of the compound of formula III

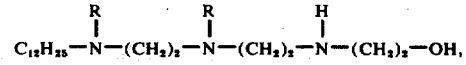

where one R is hydrogen and one R is the group —(CH$_2$)$_2$OH, with formula IV,

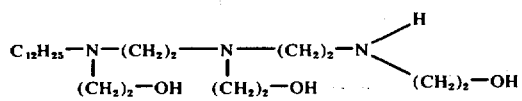

in a molar ratio of approximately 1:1 (from the components obtained according to Example 7) is diluted to 0.1% by weight of active substance and adjusted with acetic acid to a pH value of 7.6.

| Test strain | Concentration in % | \multicolumn{6}{c}{Time of action in minutes} | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | + | − | − | − | − | − |
| | 0.005 | + | + | − | − | − | − |
| | 0.001 | + | + | + | + | + | − |
| E. coli | 0.1 | − | − | − | − | − | − |
| | 0.05 | − | − | − | − | − | − |
| | 0.01 | + | + | + | + | + | + |
| | 0.005 | + | + | + | + | + | + |
| | 0.001 | + | + | + | + | + | + |
| P. vulgaris | 0.1 | + | + | − | − | − | − |
| | 0.05 | + | + | − | − | − | − |
| | 0.01 | + | + | + | + | + | + |
| | 0.005 | + | + | + | + | + | + |
| | 0.001 | + | + | + | + | + | + |
| P. aeruginosa | 0.1 | − | − | − | − | − | − |
| | 0.05 | − | − | − | − | − | − |
| | 0.01 | + | + | + | + | + | + |
| | 0.005 | + | + | + | + | + | + |
| | 0.001 | + | + | + | + | + | + |

Table 13

From 6 parts by weight of

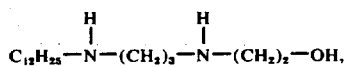

5 parts by weight of a solution, 80% by weight of which is

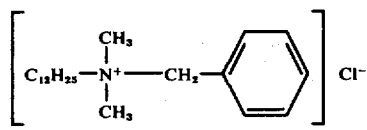

and 20% by weight of which is ethanol, 2 parts by weight of acetic acid and 87 parts by weight of water, a clear solution is prepared, whose dilution to 0.1% of active substance has a pH value of 6.0.

| Test strain | Concentration in % | \multicolumn{6}{c}{Time of action in minutes} | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | + | + | + | + | − |
| E. coli | 0.1 | − | − | − | − | − | − |
| | 0.05 | − | − | − | − | − | − |
| | 0.01 | + | − | − | − | − | − |
| | 0.005 | + | + | + | + | − | − |
| | 0.001 | + | + | + | + | + | + |
| P. vulgaris | 0.1 | + | − | − | − | − | − |
| | 0.05 | + | − | − | − | − | − |
| | 0.01 | + | + | − | − | − | − |
| | 0.005 | + | + | + | − | − | − |
| | 0.001 | + | + | + | + | + | + |
| P. aeruginosa | 0.1 | − | − | − | − | − | − |
| | 0.05 | − | − | − | − | − | − |
| | 0.01 | + | − | − | − | − | − |
| | 0.005 | + | − | − | − | − | − |
| | 0.001 | + | + | + | + | + | + |

Conservation Test (According to G. Schuster, H. Modde "Fette, Seifen, Anstrichmittel" [Fats, Soaps, Coaring Agents] 70, 169 − 174 (1968) ).

Added to 100 ml each of a silicone oil emulsion is 0.1 or 0.05 gram of

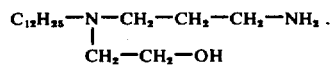

Added to this mixture is 0.5 ml of a germ suspension (mixture of C. albicans, P. aeruginosa, E. coli, P. vulgaris, S. aureus haem., S. albus, B. subtilis, A. aerogenes; with the total germ number of 2.3 × 10⁷ germs/ml). The germ number is determined immediately after contamination as well as after 24 hours, 48 hours, 1 week, 2 weeks, and 3 weeks.

| Result: | 0.1% active substance | 0.05% active substance |
|---|---|---|
| immediately | 0 germ | $2.0 \times 10^2$ germs/ml |
| after 24 hours | 0 germs | 0 germs |
| after 48 hours | 0 germs | 0 germs |
| after 1 week | 0 germs | 0 germs |
| after 2 weeks | 0 germs | 0 germs |
| after 3 weeks | 0 germs | 0 germs |

Comparative Test

The mode of operation of hexachlorophene as a disinfectant has been described in the book "Sterilisation, Desinfektion, Konservierung, Chemotherapie" (Sterilization, Disinfection, Conservation, Chemotherapy) by Wallhaeusser and Schmidt, Georg Thieme Editor, Stuttgart, 1967, page 193. Employed as a comparative substance was a mixture of equal parts by weight of hexachlorophene and a reaction product of 12 moles of ethylene oxide with tridecyl alcohol. The cited concentrations refer to the content of hexachlorophene. The pH value of the aqueous solution is 7.7.

| Test strain | Concentration in % | Time of action in minutes | | | | | |
|---|---|---|---|---|---|---|---|
| | | 1 | 2 | 5 | 10 | 20 | 30 |
| S. aureus | 0.1 | + | – | – | – | – | – |
| | 0.05 | + | – | – | – | – | – |
| | 0.01 | + | + | + | + | + | – |
| | 0.005 | + | + | + | + | + | + |
| E. coli | 1.0 | + | + | + | + | + | – |
| | 0.5 | + | + | + | + | + | + |
| P. aeruginosa | 2.0 | – | – | – | – | – | – |
| | 1.0 | + | + | + | + | + | – |
| | 0.5 | + | + | + | + | + | + |
| C. albicans | 5.0 | + | + | + | + | + | + |
| | 2.5 | + | + | + | + | + | + |
| | 1.0 | + | + | + | + | + | + |
| P. expansum | 5.0 | + | + | + | + | + | + |
| | 2.5 | + | + | + | + | + | + |
| | 1.0 | + | + | + | + | + | + |

The table shows the superiority of the inventive compound with respect to its microbiocidal efficacy.

It will be obvious to those skilled in the art that many modifications may be made within the scope of the present invention without departing from the spirit thereof, and the invention includes all such modifications.

What is claimed is:

1. A process for killing microbes which comprises contacting said microbes with a microbiocidally effective amount of a compound having the formula

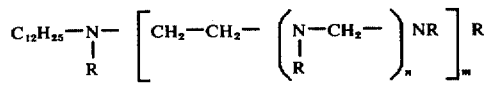

in which
n and m are 0 or 1, and n is 0 if m is 0, and
R is hydrogen or a —(CH₂)₂OH group, at least one R being a —(CH₂)₂OH group.

2. A process according to claim 1 in which the compound has the formula

3. A process according to claim 1 in which the compound has the formula

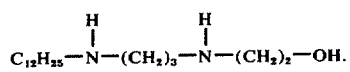

4. A process according to claim 1 in which the compound has the formula

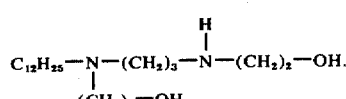

5. A process according to claim 1 in which the compound has the formula

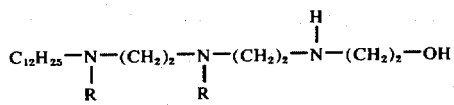

in which one R is hydrogen and one R is the —CH₂CH₂OH group.

6. A process according to claim 1 in which the compound has the formula

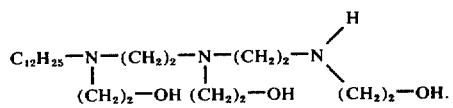

7. A process according to claim 1 in which the compound has the formula

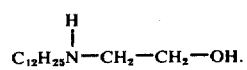

8. A microbiocidal composition comprising a carrier and a microbiocidally effective amount of a compound having the formula

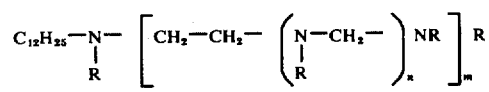

in which
n and m are 0 or 1, and n is 0 if m is 0, and
R is hydrogen or a —(CH₂)₂OH group, at least one R being a —(CH₂)₂OH group.

9. A microbiocidal composition according to claim 8 in which the compound has the formula

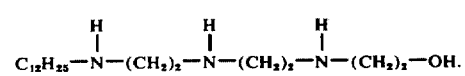

10. A microbiocidal composition according to claim 8 in which the compound has the formula

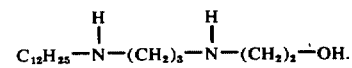

11. A microbiocidal composition according to claim 8 in which the compound has the formula

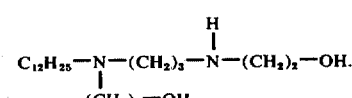

12. A microbiocidal composition according to claim 8 in which the compound has the formula

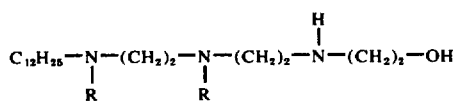
in which one R is hydrogen and one R is the —CH$_2$CH$_2$OH group.
13. A microbiocidal composition according to claim 8 in which the compound has the formula
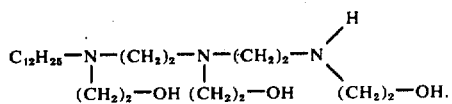
14. A microbiocidal composition according to claim 8 in which the compound has the formula
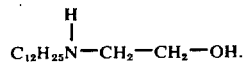
* * * * *